US012343594B2

(12) United States Patent
Wainwright

(10) Patent No.: US 12,343,594 B2
(45) Date of Patent: Jul. 1, 2025

(54) METHOD AND APPARATUS FOR MONITORING USER EFFECTIVENESS DURING OPERATION OF AN EXERCISE MACHINE

(71) Applicant: WATTBIKE IP LIMITED, Nottingham (GB)

(72) Inventor: Barney Wainwright, Nottingham (GB)

(73) Assignee: Wattbike IP Limited, Nottingham (GB)

( * ) Notice: Subject to any disclaimer, the term of this patent is extended or adjusted under 35 U.S.C. 154(b) by 928 days.

(21) Appl. No.: 17/255,845

(22) PCT Filed: Jun. 5, 2019

(86) PCT No.: PCT/GB2019/051559
§ 371 (c)(1),
(2) Date: Dec. 23, 2020

(87) PCT Pub. No.: WO2020/002871
PCT Pub. Date: Jan. 2, 2020

(65) Prior Publication Data
US 2021/0251544 A1   Aug. 19, 2021

(30) Foreign Application Priority Data
Jun. 25, 2018   (GB) ...................................... 1810397

(51) Int. Cl.
*A63B 22/06*   (2006.01)
*A63B 24/00*   (2006.01)
(Continued)

(52) U.S. Cl.
CPC ...... *A63B 24/0062* (2013.01); *A63B 22/0605* (2013.01); *G16H 50/30* (2018.01); *A63B 2024/0065* (2013.01)

(58) Field of Classification Search
None
See application file for complete search history.

(56) References Cited

U.S. PATENT DOCUMENTS 4,133,550 A * 1/1979 Brown ..................... B62M 9/04
                                                      280/238
4,463,433 A * 7/1984 Hull ...................... G01L 1/2262
                                                      702/41
(Continued)

FOREIGN PATENT DOCUMENTS

JP   2009509849 A   3/2009
JP   2012236431     12/2012
(Continued)

OTHER PUBLICATIONS

International Preliminary Report on Patentability completed Jun. 18, 2020, for International Patent Application No. PCT/GB2019/051559.
(Continued)

*Primary Examiner* — Shila Jalalzadeh Abyaneh
(74) *Attorney, Agent, or Firm* — Renner, Otto, Boisselle & Sklar, LLP

(57) ABSTRACT

A method of monitoring user effectiveness during cyclic operation of an exercise machine (10) having a pair of human limb-operable drive members (31,32) coupled for cyclic movement. The method comprises the steps of: (i) measuring and monitoring the drive force applied to the drive members (31,32) during cyclic movement of the drive members (31,32) and generating one or more force signals indicative thereof; (ii) using the one or more force signals to derive for each cycle of movement of the drive members (31,32) at least one maximum user effectiveness coefficient signal indicative of variation of force relative to a maximum force value measured for that cycle of movement and at least one minimum user effectiveness coefficient signal indicative
(Continued)

of variation in force relative to a minimum force value measured for that cycle of movement; (iii) using the maximum and minimum user effectiveness coefficient signals derived in step (ii) to generate a user effectiveness score signal that is indicative of user effectiveness in driving cyclic movement of the drive members; and (iv) using the user effectiveness score signal in recording, displaying, printing, storing, downloading, uploading or transmitting one or more indicia representative of the user effectiveness score signal.

19 Claims, 5 Drawing Sheets

(51) Int. Cl.
*G16H 50/30* (2018.01)
*A61B 5/00* (2006.01)
*A61B 5/22* (2006.01)
*G16H 40/63* (2018.01)

(56) References Cited

U.S. PATENT DOCUMENTS

| | | | | |
|---|---|---|---|---|
| 5,027,303 | A * | 6/1991 | Witte | B62J 45/421 |
| | | | | 482/901 |
| 7,833,135 | B2 * | 11/2010 | Radow | B62M 3/00 |
| | | | | 482/4 |
| 2007/0245835 | A1 * | 10/2007 | Hauschildt | A43B 3/44 |
| | | | | 73/862.391 |
| 2008/0217881 | A1 | 9/2008 | Gobillard | |
| 2010/0024590 | A1 * | 2/2010 | O'Neill | G01L 3/242 |
| | | | | 702/41 |
| 2011/0082397 | A1 | 4/2011 | Alberts | |
| 2011/0111923 | A1 * | 5/2011 | Bacanovic | A63B 22/0605 |
| | | | | 482/8 |
| 2013/0019700 | A1 * | 1/2013 | Matsumoto | G01L 5/161 |
| | | | | 73/865.4 |
| 2014/0060212 | A1 | 3/2014 | Tetsuka | |
| 2017/0334513 | A1 * | 11/2017 | Brulais | B62M 6/50 |

FOREIGN PATENT DOCUMENTS

| | | |
|---|---|---|
| JP | 2014008789 A | 1/2014 |
| WO | 2014145981 | 9/2014 |
| WO | 2017122007 A1 | 7/2017 |

OTHER PUBLICATIONS

International Search Report and Written Opinion mailed Aug. 22, 2019, for International Patent Application No. PCT/GB2019/051559.
Examination Report dated Feb. 22, 2023, for corresponding Australian Application No. 2019293144.
Examination Report dated Mar. 10, 2023, for corresponding Canadian Application No. 3,103,858.
Communication pursuant to Article 94(3) EPC dated Apr. 13, 2023, for corresponding European Application No. 19734135.7.
Office Action mailed Jan. 10, 2023, for corresponding Japanese Application No. 2020-572385.
Examination Report dispatched Jul. 15, 2022, for corresponding Indian Patent Application No. 202127003089.
Examination Report dated Jun. 29, 2022, for corresponding Russian Patent Application No. 2020141997/14.

* cited by examiner

METHOD AND APPARATUS FOR MONITORING USER EFFECTIVENESS DURING OPERATION OF AN EXERCISE MACHINE

The invention relates to a method of and apparatus for monitoring user effectiveness during cyclic operation of an exercise machine. Exercise machines having cranks or similar limb-powered members include but are not limited to bicycles (that could be recumbent and/or upright static bicycles, road or off-road bicycles, or tandems), tricycles, upper body exercise machines, rowing boats, rowing training machines and pedalos.

According to an aspect of the invention, there is provided a method of monitoring user effectiveness during cyclic operation of an exercise machine having a pair of human limb-operable drive members coupled for cyclic movement, the method comprising the steps of:
(i) measuring and monitoring the drive force applied to the drive members during cyclic movement of the drive members and generating one or more force signals indicative thereof;
(ii) using one or more force signals to derive for each cycle of movement of the drive members at least one maximum user effectiveness coefficient signal indicative of variation of force relative to a maximum force value measured for that cycle of movement and at least one minimum user effectiveness coefficient signal indicative of variation in force relative to a minimum force value measured for that cycle of movement;
(iii) using the maximum and minimum user effectiveness coefficient signals derived in step (ii) to generate a user effectiveness score signal that is indicative of user effectiveness in driving cyclic movement of the drive members; and
(iv) using the user effectiveness score signal in recording, displaying, printing, storing, downloading, uploading or transmitting one or more indicia representative of the user effectiveness score signal.

The invention allows the calculation of a user effectiveness score that may be displayed to a user. The score is such that it is reduced in the event of greater variations of force about (i.e. relative to) the maximum and/or minimum force values measured for each cycle of movement during cyclic movement of the drive members. The score can be provided immediately to a user of the exercise machine, who can use the feedback to work on achieving optimal effectiveness.

Preferably the step (i) of measuring and monitoring the drive force applied to the drive members includes periodically causing one or more force sensor that is operatively coupled to the drive members to generate the one or more force signals.

Conveniently the one or more force sensor senses the force acting on or in a drive component that is driven by the drive members.

Further conveniently the drive component is a drive chain and the one or more force sensor measures tension in the drive chain and generates one or more signal indicative thereof.

Preferably the periodicity of generation of the force signals is 100 Hz.

In the embodiments the step (ii) includes the step of, in respect of at least one cycle of movement, or part thereof, of one of the said drive members during which the said drive member provides a dominant proportion of the drive force, (iia) comparing the magnitude of a plurality of the periodically generated force signals generated during the at least one cycle of movement or part thereof with the maximum magnitude force signal generated during the said cycle of movement or part thereof and based on the comparison generating the at least one maximum user effectiveness signal; and (iib) comparing the magnitudes of a plurality of the periodically generated force signals generated during the at least one cycle of movement or part thereof with the minimum magnitude force signal generated during the said cycle of movement or part thereof and based on the comparison generating the at least one minimum user effectiveness signal.

Further preferably the method may include repeating steps (iia) and (iib) in respect of at least one cycle of movement, or part thereof, of the other said drive member during which the said other drive member provides a dominant proportion of the drive force.

Conventionally, efficiency has been calculated as the ratio of work done to energy expended. Remaining efficient by conserving energy or by maximising the work done per unit of energy expended is key to success in certain sports, such as endurance and other forms of cycling, triathlon, athletics and many forms of rowing.

In cycling, forces, torques or power delivered by the cyclist to the pedals of a bicycle can be measured using force pedals or instrumented (i.e. force or torque measuring) cranks.

A comparatively even distribution of torque about the crank axis throughout the crank cycle has for many years been promoted as an "efficient" technique.

However, simply knowing the efficiency is not as valuable as finding out how effective the pedalling technique is. The invention allows the relationship between (a) the drive force applied to the drive members of an exercise machine and (b) user effectiveness during cyclic operation of the drive members to be assessed and thus complements force, torque and/or power measurements, rendering them more useful to coaches and athletes.

During cycling, lower limb movement parallel to the sagittal plane is constrained to a circular path by the geometry of the cranks and pedals of a bicycle. Within these constraints, an experienced cyclist can vary his/her pedalling technique by changing the kinematics of his/her lower limbs (e.g. thigh, calf and foot) and activation of muscles. Technique in cycling can be assessed through measurement of joint kinematics and muscle activation patterns, but measurements of these kinds call for specialist equipment and, therefore, usually are only available to elite athletes.

To promote an optimal pedalling technique, it is useful for a cyclist to monitor how he/she turns the cranks while riding, and also to receive immediate, real-time feedback on how effective the cranking/pedalling technique is. Current static bicycles can display power, heart rate and cadence data, as well as certain other cycling parameters, in real time to give riders in-depth and accurate feedback. Similar data are available when riding a road or off-road bicycle fitted with instrumented cranks or force pedals. Heart rate data can be generated in a variety of ways, e.g. through use of a chest strap sensor. Similar measuring arrangements may be employed in other cyclic exercise products such as those listed herein.

It is known to provide information on the cranking or pedalling technique of a cyclist using a so-called "polar view™" display or plot. The polar view™ display was developed by the Applicant, and associated entities, and is marketed exclusively by the Applicant's associated entity, Wattbike Limited.

The polar view™ is generated from force measurements recorded at a sampling rate of, for example, 100 Hz in the drive train of the Wattbike® 10 and Wattbike Atom™ 50 static bicycles shown in FIGS. 1 and 4.

A sample polar view™ 11 is shown in FIG. 2 in which the polar grid 12 represents 360° of cyclic motion of pedals cranks of a Wattbike® 10 or Wattbike Atom™ 50.

The thickened portions 12*a*, 12*b* of the grid 12 correspond respectively to the downstrokes of the right and left pedals of the Wattbike® 10 or Wattbike Atom™ 50. Plot lines 13 are plural in number and represent multiple revolutions of the pedal cranks. The plot lines in the right-hand section 13*a*, to one side of line A-A in FIG. 2, represent the drive force applied to the pedal cranks during the downstroke of the right crank, when the dominant drive force applied to the pedal cranks is applied via the right crank. The plot lines in the left-hand section 13*b*, to the other side of line A-A in FIG. 2, represent the drive force applied to the pedal cranks during the downstroke of the left crank, when the dominant drive force applied to the pedal cranks is applied via the left crank.

As is known in the cycling art, the maximum force applied via a pedal crank occurs when each crank has travelled approximately ⅓ of the way from its top dead centre (tdc) position in a complete 360° revolution of the crank—typically between 100° and 120° from the top dead centre position. The point of maximum force application is illustrated in the polar view™ shown in FIG. 2 by line 14 in respect of the right crank and line 16 in respect of the left crank.

The polar view™ 11 may be plotted using a printer but is more commonly displayed by way of a real-time-display connected to the electronics of the Wattbike® 10 or the Wattbike Atom™ 50, the display being connected to the electronics by means of wires or by a wireless communications protocol. Such a display updates on a continuous basis. The displayed maximum force angle lines 14,16 relate to the most recently completed pedal revolution from among the plot lines.

A user of the Wattbike® 10 or the Wattbike Atom™ 50 may view the polar view™ 11 whilst exercising and may seek in real time to optimise his/her pedalling technique by improving the appearance of the polar view™ 11 data.

in particular, the user may seek one or more of the following improvements:
making the angle subtended between the maximum force angle lines 14,16 as close as possible to 180°, thereby assuring consistency of effort between the left and right legs;
minimising the differences between the least force sections 17,18 of the polar view™ plot lines 13 on the one hand and the average force sections 19 on the other hand; and
(in the case of sprint cyclists, and less importantly for endurance cyclists) maximising the plot line amplitude (and hence the maximum force applied) by causing the plot lines 13 to reach as far as possible along the maximum force angle lines 14,16.

The polar view™ 11 has proved, in conjunction with other features of the Wattbike® products 10, 50, to be a highly effective training aid. The feedback achieved through use of the polar view™ is, however, essentially visual and therefore relies on estimations made by the user or by a coach viewing the polar view™ data. The invention usefully augments or replaces a user's reliance on the polar view™ during use of the Wattbike® 10 or the Wattbike Atom™ 50 in that it provides an immediate score indicative of the user's pedalling efficiency and thus removes the need for visual analysis of the polar view™ that might be inaccurate because of factors such as:
the fatigue level of the user when he/she is assessing his/her own performance;
the fact that some of the polar view™ 11 data are transitory owing to the real time updating characteristic described above; and
periods of intense effort making it difficult to concentrate on the lines of the polar view™ 11 display.

The invention also produces benefits in or in conjunction with a variety of other cyclic exercise or training machines, including but not limited to those mentioned herein.

In preferred embodiments, the human limb-operable drive members are coupled for cyclic movement to drive a drive train that transfers or dissipates cyclic effort.

In such embodiments, the drive force applied to the drive members during cyclic movement of the drive members may be measured and monitored by measuring the force generated in the drive train at at least one location.

In other embodiments, however, the drive force applied to the drive members during cyclic movement of the drive members may be measured and monitored through the use of force pedals and/or instrumented cranks, or through the use of measuring devices located in a wheel hub or in a user's shoes, insoles or shoe attachable cleats.

The invention is not limited to use on a static bicycle or even more conventional bicycles that are capable of locomotion. The method of the invention is instead applicable to, and is of potentially benefit in, all human-powered exercise machines having pairs of human limb-operable cranks or other limb-powered members. For example, an athlete using an upper body exercise machine may benefit from knowing the effectiveness of rotation of the cranks of such a machine while working on upper body fitness. The invention also is of potential benefit in relation to manually operated windlasses and capstans (and training devices that simulate the actions of such devices) as are encountered in yachts and dinghies, especially those intended for racing. The invention, furthermore, is of potential benefit in working boats and rowing simulators such as the so-called "static tank", in which each of a pair of oars or paddles may be considered as a human limb-operable drive member as referred to herein, and the kinematic chain extending from the hand grip of such an oar to water or another liquid in which the oar blade is movable as a drive train as referred to herein. Yet a further class of exercise machine in which the method and apparatus of the invention is potentially of use includes elliptical trainers, cross-country skiing simulators, stair climber machines, steppers, pedalos and vertical climbing simulators, all of which include human limb-operable drive members.

Preferably, therefore, the drive members are selected from the list comprising pedal cranks, upper body exercise cranks, capstan cranks, windlass cranks, static tank oars, rowing boat oars, stepper or stair climber pedals, elliptical trainer pedals and/or handgrips, skilling simulator pedals and/or handgrips, climbing simulator pedals and/or handgrips, or pedalo pedals. In other words, as stated, the method of the invention is applied in respect of a range of exercise machine types.

Preferably, the method further includes the step of modifying cyclic operation of the drive members based on the user effectiveness score.

Modifying cyclic operation of the cranks or other drive members amounts to the incorporation of user feedback into the use of an exercise machine. This is believed to be highly effective in improving athletic performance, regardless of the fitness level of the user.

It is an advantage if the exercise machine includes a respective pedal or handle that is rotatably secured to each said drive member, the drive members being coupled to drive rotation of a drive wheel and the drive members mutually subtending an angle of 180°.

More specifically, the exercise machine preferably is or includes a static exercise machine that includes pedals in preference to handles. As noted above, however, the method of the invention is equally applicable to a range of hand-powered exercise machines.

In such embodiments, the drive wheel may include one or more sensors that facilitates the generation of a signal at top dead centre and bottom dead centre positions of the drive members so as to allow the rotational positions of the drive members to be monitored during cyclic movement thereof.

More specifically, the drive wheel may include one or more sensors that facilitates the generation of a signal at top dead centre and bottom dead centre positions of the drive members so as to allow the rotational positions of the drive members to be monitored during cyclic movement thereof.

The exercise machine may be a static bicycle. The pedals of such a machine optionally may be equipped with toe clips and straps or may be of a clipless type, including pedals intended for force-transferring gripping of shoe cleats.

A static bicycle is especially useful for indoor cycle training both in general terms and when weather conditions are not ideal. The controlled environment of indoor cycling allows the cyclist to isolate and concentrate on specific areas of cycling fitness and technique, which the cyclist may not be able to do when cycling on roads. Nowadays, moreover, amateur and professional cyclists often find it beneficial to include indoor static bicycle use in their training programmes, even during periods of good weather.

In embodiments where the drive members are coupled for cyclic movement to drive a drive train that transfers or dissipates cyclic effort, the drive train may drive a fan that forces air in a chamber via an exit aperture that resists the passage of air thereby to dissipate cyclic effort. This is the primary means of cyclic effort dissipation used in the Wattbike® 10 referred to above.

Preferably, the dimensions of the exit aperture are adjustable to permit adjustment of the extent to which the exit aperture resists the passage of air, the method including the step of adjusting the dimensions of the exit aperture.

In other embodiments where the drive members are coupled for cyclic movement to drive a drive train to transfer or dissipate cyclic effort, the drive train may include a magnetic and/or electromagnetic resistor 62 of cyclic effort, the method including the step of switching or adjusting cyclic resistance using the magnetic and/or electromagnetic resistor 62. This is the primary means of cyclic effort dissipation used in the Wattbike Atom™ 50.

Preferably, in such embodiments, the degree of resistance provided by such a resistor may be adjusted, e.g. by moving a magnet mounted by way of a screw thread selectively closer to or further away from an element of the drive train.

Other cyclic-based exercise machines may, within the scope of the invention, use other mechanisms for dissipating cyclic effort.

In embodiments wherein a dominant proportion of user cyclic effort in driving cyclic movement of the drive members alternates between left and right limbs once per cycle of movement of the drive members, step (i) includes allocating drive force signal values measured during a cycle of movement to one or other of the drive members based on points of load alternation during the cycle of movement, step (ii) includes deriving maximum and minimum user effectiveness coefficient signals for each drive member, and step (iii) includes using the maximum and minimum user effectiveness coefficient signals derived for each drive member in step (ii) to generate a user effectiveness score signal for each drive member before generating an overall user effectiveness score based on the mean of the user effectiveness score signal values generated for each drive member.

Allocating a numerical representation of the user effectiveness helps the user of the exercise machine to know how close his/her technique is to a technique corresponding to optimal effectiveness.

Preferably, the step of generating a user effectiveness score signal in step (iii) additionally involves using a predetermined weighting factor with the maximum and minimum user effectiveness coefficient signals calculated in step (ii), the weighting factor being based on a ratio for the exercise machine between the effective force applied to the drive members and the total force applied to the drive members that is required to achieve the effective force.

The step of generating a user effectiveness score signal in step (iii) may also additionally involve using a predetermined moderation factor so that the user effectiveness score for each drive member falls within an optimum range between 70 and 80.

The maximum user effectiveness coefficient may be calculated as:

$$coeff_{max} = \frac{\text{mean max force}}{\text{maximum force value}}$$

where the mean max force is the mean value of the drive force signal values measured for that cycle of movement over a predetermined segment of the cycle in which the maximum force signal value is the median data point of the drive force signal values measured in the segment. Such measurement may occur through operation of the one or more sensors and generation of a plurality of force signal outputs.

In such embodiments, the minimum user effectiveness coefficient may be calculated as:

$$coeff_{min} = \frac{\text{minimum force value}}{\text{mean min force}}$$

where the mean min force is the mean value of the drive force signal values measured for that cycle of movement over a predetermined segment of the cycle in which the minimum force signal value is the median data point of the drive force values measured in the segment. Such measurement again may occur through operation of the one or more sensors and the generation of plural force signal outputs.

The maximum and minimum user effectiveness coefficients reflect the shape of the maximum and minimum drive force profiles. In the case of a bicycle (whether a static bicycle or a conventional bicycle), the optimum drive force profile defines a relatively gentle curve through the maximum and minimum drive force value measured for each cycle of movement. This results in higher maximum and minimum user effectiveness coefficient values and thus a higher overall user effectiveness score.

In embodiments where the exercise machine includes drive members coupled to drive rotation of a drive wheel 61 such that the drive members mutually subtend an angle of 180°, the mean max force and the mean min force are preferably determined based on drive force values measured over segments of 45°. As indicated the segments are centered respectively on the maximum and minimum force values in the crank, etc., cycle.

Preferably, the method includes the step of generating a polar view™ illustrating the drive force applied to the drive members as it is allocated to the drive members for each cycle of movement.

The ability to monitor rotation of the drive members as the exercise machine is used can be shown as a force curve in the form of a polar view™ plot. The polar view™ plot illustrates the variable drive force applied via the drive members and the positions of the drive members during force application.

In order to permit the calculation of an accurate representation of the user effectiveness in the form of the overall user effectiveness score, the drive force applied to the drive members is preferably measured at a frequency of about 100 Hz.

In embodiments where the exercise machine includes a drive train having a drive chain, step (i) may include measuring tension in the chain and generating one or more signals indicative thereof.

In embodiments where the exercise machine includes a drive train including an axle, step (i) may include measuring the value of torque in the axle and generating one or more signals indicative thereof.

The method may include generating plural indicia representative of the user effectiveness score over a monitoring period, the method optionally including the step of analysing the effectiveness score signals and detecting changes in the effectiveness score signal values during the monitoring period.

Furthermore, the method may include the step of recording, transmitting, downloading, uploading, storing, printing or displaying data indicative of usage of the exercise machine.

The method may include the displaying, printing, storing, downloading or transmitting of a user training programme.

Preferably, the user training programme can be modified based on the user effectiveness score for one or more cycles of movement of the drive members.

Having a user training programme provides guidance to the user. Adjusting the training programme based on the user effectiveness score creates a personalised training regime and results in a more productive workout for the user.

One or more programmable device may be used to generate the user effectiveness score. Other types of calculating device, that need not be programmable, may additionally or alternatively be used. Examples include but are not limited to Op Amp circuits.

Preferably the one or more programmable or other calculating device includes a display and is operably connected to the exercise machine. Additionally, or alternatively, the one or more programmable or other calculating device may be capable of producing a different sensory output, such as but not limited to an audible output.

A user able to see or e.g. hear an output that is indicative of the user effectiveness score generated by a programmable or other calculating device will benefit from having immediate real time feedback on the cyclic effort he/she is putting in and whether the way he/she is rotating the crank at that particular moment is effective.

Advantageously, the method includes the step of generating one or more user power value signals indicative of power generated through operation of the drive members, and recording, displaying, printing, storing, downloading, uploading or transmitting one or more user power values.

Such "training with power" provides a quantitative number that tells a user exactly how much power he/she generates during exercise. This is valuable information the measurement of which can be made independent of external factors such as fatigue, hydration and temperature. An indication of generated power allows the athlete to be confident of training within designated training zones such as those familiar to competitive cyclists.

Preferably the exercise machine includes at least one receiver of heart rate data signals, the method including the step of using one or more of a chest strap, wrist strap, ankle strap or finger clip transmitting heart rate sensor in the generation of one or more user heart rate values.

It is also advantageous that the method includes the steps of generating one or more signals indicative of user heart rate values and recording, displaying, printing, storing, downloading, uploading or transmitting one or more user heart rate values generated from such signals. Such values can be displayed at the same time as user power data as described above. The Applicant has found this to provide for particularly effective training techniques.

Heart rate is a useful indicator for determining the ideal intensity ranges for workouts because the heart rate indicates the body's response to effort. Monitoring of heart rate data moreover can provide real-time indications of the effects of dehydration and fatigue; and, furthermore, can be very helpful when seeking to improve the fitness of a person who is recovering from illness, surgery or other forms of medical treatment. Exercise heart rate data additionally can be used to monitor e.g. the response of an individual to certain types of medication. It is also beneficial when assessing the fitness level of an individual as may be required in selection processes for certain jobs such as those in military, law enforcement, fire service and civil defence organisations.

Preferably, the user effectiveness score is generated using an application that can be downloaded or accessed via Cloud-based computing.

As is well known, Cloud-based computing allows access to application, analysis software and user data through the internet with good flexibility and accessibility without consuming a significant percentage of the memory capacity of a programmable device such as one used to implement the steps of the method of the invention.

According to another aspect of the invention, there is provided an exercise machine comprising a pair of human limb-operated drive members coupled for cyclic movement, and an electronic device, having at least one sensory indicator, operatively connected to the exercise machine, the exercise machine and electronic device generating a said user effectiveness score by implementing a method according to the invention as defined herein and outputting the user effectiveness score via the sensory indicator.

Preferably the sensory indicator is a visible display and the step of outputting the user effectiveness score may include displaying the user effectiveness score using the display. Additionally, or alternatively, the sensory indicator may be or may include an audible indicator and the step of outputting the user effectiveness score may include generating an audible indication of the user effectiveness score using the audible indicator.

Preferably, the electronic device is selected from the list including a laptop or desktop computer, a so-called "tablet", a smartphone or a person digital assistant (PDA). Additionally, or alternatively, the electronic device may be or may include a dedicated monitoring device that is operatively connected to the exercise machine.

Advantageously, the exercise machine is configured as a static exercise bicycle including a respective pedal rotatably secured to each drive member. The exercise machine however may be configured as any of a range of other types, including but not limited to those listed herein.

There now follows a description of preferred embodiments of the invention, byway of non-limiting examples, with reference to the accompanying drawings in which.

Preferences and options for a given aspect, feature or parameter of the invention should, unless the context indicates otherwise, be regarded as having been disclosed in combination with any and all preferences and options for all other aspects, features and parameters of the invention.

As used herein "signals" relates predominantly to electrical signals, and references to the value or magnitude of such signals are references to parameters such as voltages which vary in dependence on the outputs of the sensors that generate the signals. It is however possible to perform the method described herein using signals other than electrical ones. Optical, magnetic and audio signals at lest in some embodiments may instead be employed.

An embodiment of the invention will now be described with reference to a method of monitoring user effectiveness during operation of an exercise machine in the form of a Wattbike® static exercise machine 10. The static exercise machine could, alternatively, be another type of static bicycle such as the Wattbike Atom™ 50 shown in FIG. 4, a yacht capstan or windlass trainer, a stair climber or stepper, an elliptical trainer, a cross-country skiing simulator, a climbing simulator, an upper body exercise machine or a static tank.

Moreover, as noted herein, the method of the invention is useable in various mobile apparatuses such as road or off-road bicycles, rowing boats and features (e.g. windlasses) of sailing boats. The following description relating to a particular form of static bicycle, therefore, is presented as an example only and does not limit the scope of the invention.

Figure 1:
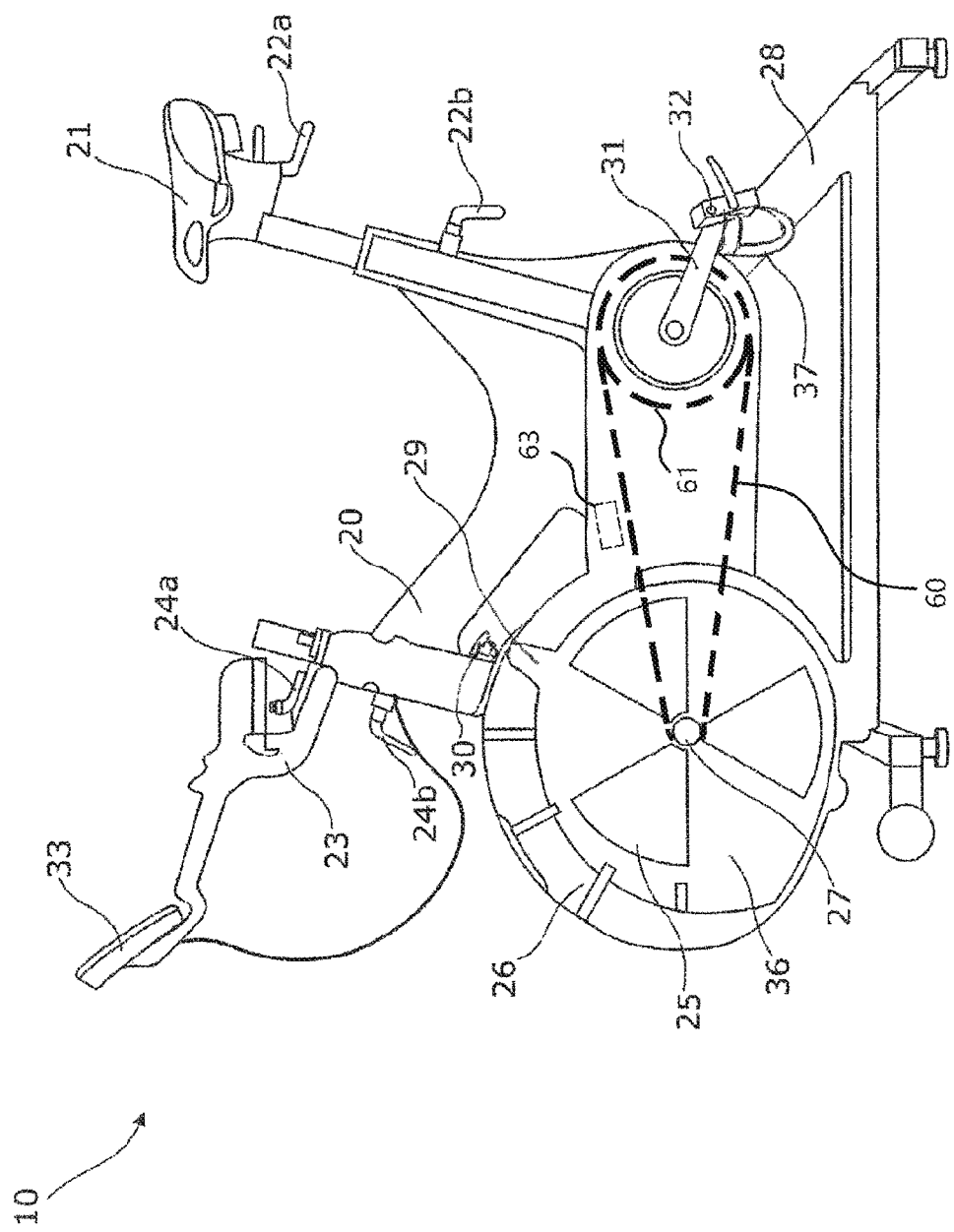
FIG. 1 shows a first embodiment of an exercise machine in the form of a Wattbike®.

A Wattbike® 10 is shown in FIG. 1. The Wattbike® 10 has a bicycle-like frame 20 with a seat 21, the position of which ca be adjusted using seat adjustment levers 22a, 22b; and handlebars 23, the position of which can be adjusted using handlebar adjustment levers 24a, 24b. The Wattbike® 10 has a front wheel guard 26 housing a flywheel that is not visible in FIG. 1 but is arranged to be rotatable about a horizontal axis coinciding with the centre 27 of the essentially circular housing 26. The Wattbike® 10 includes a support stand 28 where a rear wheel of a bicycle is normally located. The support stand 28 includes floor-engaging limits 28a, 28b that respectively extend to either side of a longitudinal centre plane of the Wattbike 10 to stabilise the machine against lateral tilting.

As is visible in the preferred embodiment each limb 28a, 28b includes an optional, downwardly extending, floor-engaging foot. The support stand 28 includes a rigid, forwardly extending frame member 30 that at its forwardmost end underlies and is fixed to the wheel guard 26. Further floor-engaging limbs 30a, 30b extend laterally from the member 30 and also may include optional floor-engaging feet. The support frame elements are rigidly secured together and provide for highly stable supporting of the operative parts of the machine 10.

At the lower section of the frame 20, the Wattbike® 10 includes a pair of drive members in the form of pedal cranks 31. In the case of other static exercise machines, the drive members could include, for example, upper body exercise cranks, capstan cranks, windlass cranks, static tank oars or rowing boat oars.

Each pedal crank 31 has a pedal 32 rotatably secured at an end. In the case of an upper body exercise machine, handles are connected to the upper body exercise cranks instead of pedals.

The pedals 32 shown in FIG. 1 are equipped with toe clip and strap combinations 37 that assist a user of the Wattbike® 10 to expend energy throughout cyclic movement of the pedal cranks 31. The reverse sides of the pedals 32 to those supporting the toe clip and strap combinations 37 are formed as so-called "clipless" pedals that can accommodate cleats attached to a user's cycling shoe.

The principles and nature of toe clips, straps and clipless pedals are well known in the cycling art and do not require detailed description herein.

Variations on the illustrated support frame, crank pedal designs are possible within the scope of the invention, as would occur to the person skilled in the art.

The pedal cranks 31 are coupled via a gear wheel so as to mutually subtend an angle of 180° such that when one of pedal cranks 31 is located at a top dead centre position, the other pedal crank 31 is located at a bottom dead centre position, and vice versa.

The gear wheel is coupled to the flywheel located in the front wheel guard 26 by means of an endless drive chain extending around the gear wheel and around a toothed sprocket mounted on the flywheel. The gearwheel, endless drive chain and toothed sprocket define a drive train that transfers cyclic effort from the pedal cranks 31 to the flywheel, cyclic movement of the pedals cranks 31 driving rotation of the gear wheel which in turn drives rotation of the flywheel via the endless drive chain and toothed sprocket.

A series of regularly spaced, radial fan blades are secured to the flywheel and the side of the wheel guard 26 that is visible in FIG. 1 includes a series of three sector-shaped grilles 25 via which air is drawn inside the volume enclosed by the wheel guard 26. Such air movement, together with the inertia of the flywheel, provides resistance to rotation of the flywheel and simulates the resistance experienced when riding a conventional bicycle outdoors. The wheel guard 26 includes one or more exit apertures via which air drawn inside the wheel guard 26 is expelled as a result of motion of the flywheel.

The front wheel guard 26 has an airbrake gear lever 29 that allows adjustment of the resistance level of the flywheel. Movement of the airbrake gear lever 29 causes rotation of a series of sector-shaped shutters 36 connected to it so as, selectively and progressively, to cover or uncover the grilles 25, regulating the flow of air entering the flywheel. Uncovering the grilles 25 increases the flow of air, increasing resistance and hence simulating riding a conventional bicycle in a higher gear than when the grilles 25 are covered to a greater degree.

Additionally, a magnetic climb lever 30 is secured to the front wheel guard 26. The magnetic climb lever 30 adjusts resistance magnets that act to resist and thereby slow rotation of the flywheel, that is made from or includes e.g. one or more ferromagnetic materials. The magnets are secured to one or more screw threads attached to the climb lever 30 and are moveable towards and away from the flywheel using the magnetic climb lever 30 in order to adjust the resistance created by the magnets. The magnetic climb lever 30 rotates and is marked with different resistance levels, allowing the user to recreate the feeling of riding on flat ground or climbing a hill while cycling.

Figure 4:
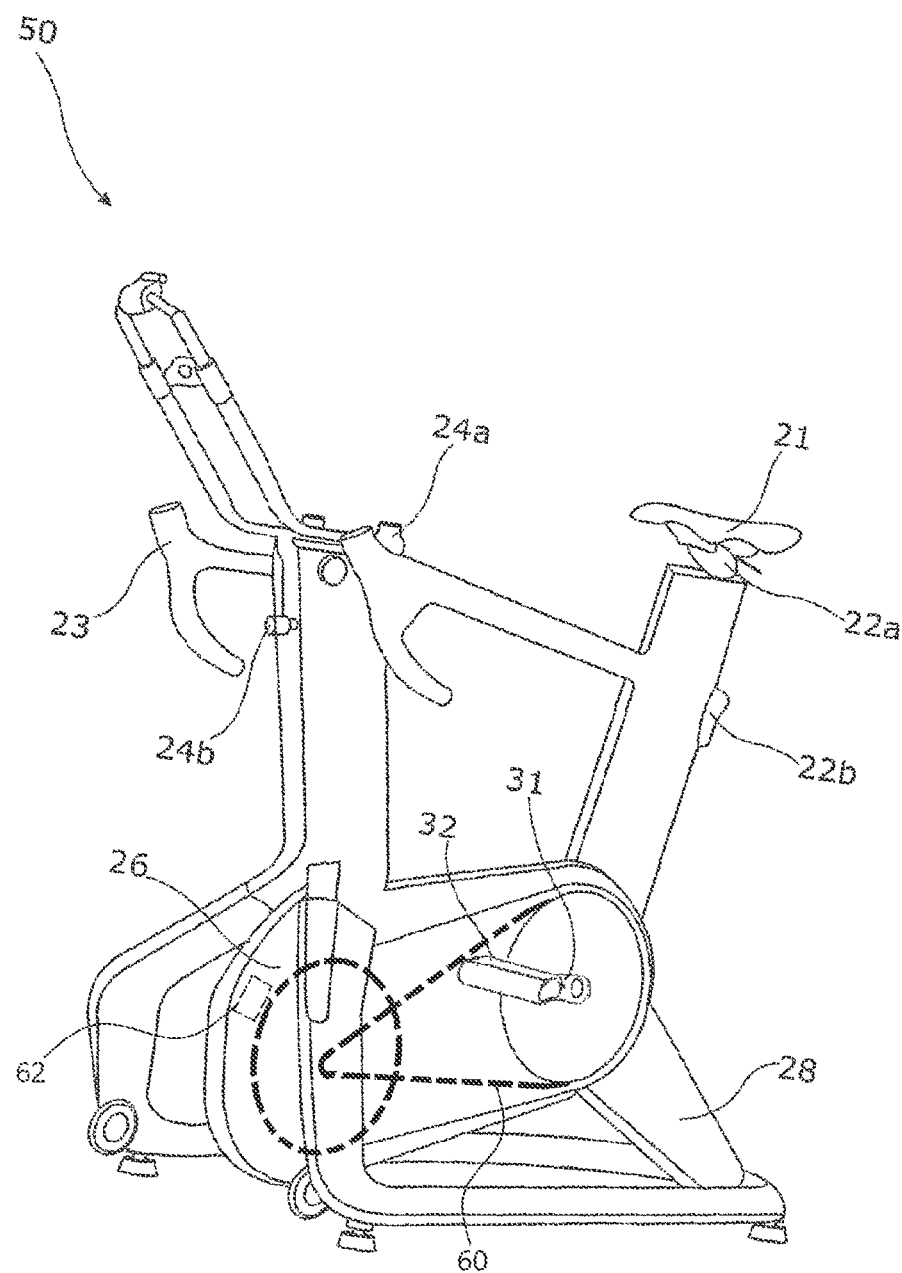
FIG. 4 shows a second embodiment of an exercise machine in the form of a Wattbike Atom™.

Referring to FIG. 4, it can be seen that the Wattbike Atom™ 50 also includes a bicycle-like frame 20 with a seat 21, the position of which can be adjusted via adjustment mechanisms 22a,22b; and handlebars 23, the position of which can be adjusted via adjustment mechanisms 24a,24b. The Wattbike Atom™ 50 includes a front wheel guard 26 housing a pair of flywheel discs that are not visible but are arranged to be rotatable about a horizontal axis. The Wattbike Atom™ 50 includes a support stand 28 where a rear wheel of a bicycle is normally located. The FIG. 4 support stand 28 while of a different design from support stand 28 in FIG. 1 is functionally similar to the FIG. 1 stand. In view of this the FIG. 4 support stand 28 is not described in detail, its construction and functioning being apparent from visual inspection of FIG. 4.

At the lower section of the frame 20, the Wattbike Atom™ 50 includes a pair of drive members in the form of pedal cranks 31, pedals 32 being rotatably coupled to the ends of the pedal cranks 31.

The configuration of the pedals 32 and the drive train coupling the pedal cranks 31 to the flywheel in order to drive rotation of the flywheel on cyclic movement of the pedal cranks 31 is the same as that employed in the Wattbike® 10 and so will not be described again in detail.

As opposed to the use of grilles and shutters, the Wattbike Atom™ 50 includes a resistance mechanism in the form of one or more permanent magnets mounted in the front wheel guard 26 in order to resist rotation of the flywheels at least one of which is made from or includes one or more e.g. ferromagnetic materials. The magnets are mounted on a screw threadedly engaged in the frame and a motor is provided in order to drive rotation of the screw. Depending on the direction of driving such driving selectively moves the magnets into or out of a gap between the pair of flywheels and thereby moves the magnets towards and away from magnetic rims of the flywheels in order to increase or reduce the resistance provided by the magnets.

In other embodiments, it is envisaged that one or more electromagnets may be used in place of one or more permanent magnets.

Both the Wattbike® 10 and the Wattbike Atom™ 50 includes a measuring unit to measure the drive force applied to the pedal cranks 31 during cyclic movement thereof, the measuring unit measuring the drive force by measuring tension in the endless drive chain 60. The measuring unit includes an arm applied to the endless drive chain, the arm pressing slightly on the side of the chain 60 and the measuring unit further including a measuring sensor 63 to measure the restoring force applied by the chain to the arm, that tends to resist pressing by the arm. Preferably, the measuring unit measures the restoring force applied by the chain to the arm at a sampling rate of 100 Hz.

The measuring unit is coupled to a sensor that in the illustrated embodiments takes the form of a magnetic field sensor positioned in a stationary location on the frame relative to the gear wheel. A pair of sensor pieces in the form of magnets are attached to the gear wheel, the sensor pieces being located on the gear wheel so as to pass the sensor on rotation of the gearwheel, the sensor generating a signal on detection of a passing sensor piece. This enables the measuring unit to calculate the speed of rotation of the gearwheel.

In order embodiments, a pair of sensors may be located in stationary locations relative to the gear wheel and at least one sensor piece may be attached to the gear wheel. In yet further embodiments, the positions of the sensor(s) and sensor piece(s) may be reversed, the sensor(s) being mounted on the gear wheel and the sensor piece(s) being mounted on the frame.

The sensor pieces are located on the gear wheel so as cause the sensor to generate signals at 180° intervals. More specifically, by appropriate positioning of the sensor pieces on the gearwheel, the sensor generates a first signal when one of the pedal cranks 31 is located at a top dead centre position and the other of the pedal cranks 31 is located at a bottom dead centre position, and a second signal when the one pedal crank 31 is located at the bottom dead centre position and the other of the pedal cranks 31 is located at the top centre position. This allows the measuring unit to reliably determine the temporal positions of the pedal cranks 31, based on the calculated speed of rotation of the gear wheel, each time the drive force applied to the pedals cranks 31 is measured.

Since the lengths of the pedal cranks 31 is fixed, the measuring unit is able readily to calculate the torque that a user applies via the pedals 32 and the pedal cranks 31 directly from the measured drive force values.

As the force on the endless drive chain is derived from user input and all the resistance is applied to one and the same axle of the Wattbike® 10 or the Wattbike Atom™ 50, the measuring unit is able to measure the power output of the user, as influenced by the resistance to rotation of the flywheel(s).

The Wattbike® 10 shown in FIG. 1 is controlled by means of a programmable or non-programmable device 33 mounted at the front of the frame 20, near the handlebars 23. The device 33 is operatively connected to the measuring unit of the Wattbike® by means of a wired connection or a wireless communications protocol.

Figure 3:
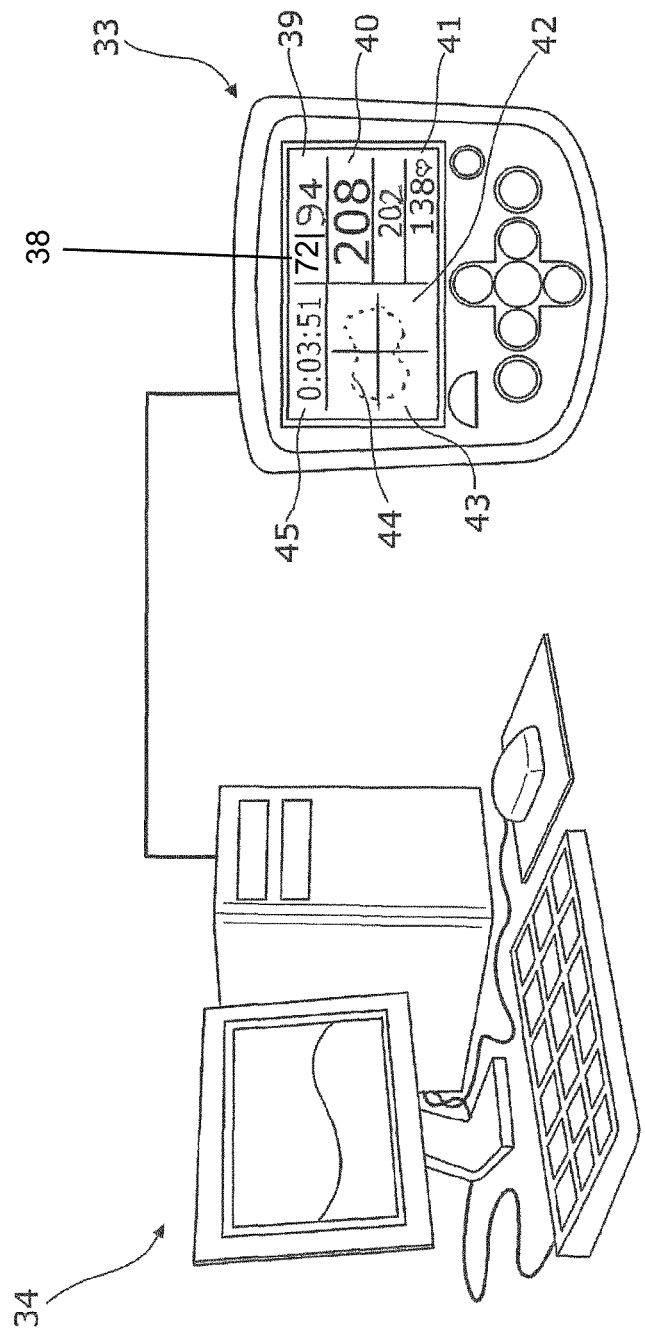
FIG. 3 is a front view of a display of a programmable device according to an embodiment of the invention, displaying a user effectiveness score, connected to a computer.

FIG. 3 shows a front view of the device 33 connected to a desktop computer 34. The programmable device 33 may also be operatively connected to a laptop, tablet, smartphone or a personal digital assistant (PDA) or in some embodiments it may be used in a stand-alone mode that does not involve connection to a further device. When the device 33 is so connected the connection may be via one or more wires or wirelessly using a near-field communications protocol such as but not limited to Bluetooth. Data can be transmitted to the desktop computer 34 when present for displaying, printing, storing, recording, downloading and uploading to, for example, the Cloud.

Additionally, a user training programme can be displayed, printed, stored, downloaded or transmitted via the programmable device 33, a connected computer such as the desktop computer 34 and/or another device.

The Wattbike Atom™ 50 shown in FIG. 4 is controlled by means of a programmable device in the form of a tablet or smart phone (not shown), which may be secured between mount elements 52a, 52b at the front of the frame 20, above the handlebars 23. At least one of the mount elements 52a, 52b is slideable, on elements forming part of the frame 20, towards and away from the other in order to permit clamping of a tablet or smartphone between the mount elements 52a, 52b. The programmable device is operatively coupled to the measuring unit of the Wattbike Atom™ 50 by means of a wireless communications protocol.

In the case of the Wattbike Atom™ 50, data can too be transmitted to a desktop computer for displaying, printing, storing, recording, downloading and uploading to, for example, the Cloud. Similarly, a user training programme can be displayed, printed, stored, downloaded or transmitted via the programmable device.

The programmable device of both the Wattbike® 10 and the Wattbike Atom™ 50 is configured to receive data pertaining to the drive force measurements and the associated temporal positions of the pedal cranks 31.

The double action of a user's legs on the pedal cranks 31, pressing with the left and recovering with the right or pressing with the right and recovering with the left, gives rise to an aggregated drive force applied to the endless drive chain that drives rotation of the flywheel(s). The device 33 or another device to which it is connected is configured to allocate the aggregated drive force to the left or right pedal crank 31 depending on which leg is providing the dominant proportion of the drive force, the signals generated by the sensor when the pedal cranks 31 are located in their top dead centre and bottom dead centre positions signifying load alternation between the left and right pedals cranks 31.

The device 33 or another device is configured to use the received data to calculate maximum and minimum user coefficient signals for each of the left and right pedal cranks 31.

The maximum user coefficient for each of the left and right pedal cranks 31 is calculated according to the following equation:

$$coeff_{max} = \frac{\text{mean max force}}{\text{maximum force value}}$$

where the mean max force is the mean value of the drive force signal values generated by the force sensor for that cycle of movement over a segment of 45° of the cycle in which the maximum force value signal generated is the median data point of the drive force values measured in the segment.

The minimum user coefficient for each of the left and right pedal cranks 31 is calculated according to the following equation:

$$coeff_{min} = \frac{\text{minimum force value}}{\text{mean min force}}$$

where the mean min force is the mean value of the drive force signal values generated by the force sensor for that cycle of movement over a segment of 45° of the cycle in which the minimum force value signal is the median data point of the drive force signal values measured in the segment.

As is apparent the maximum and minimum user coefficient signals are generated by comparing the maximum and "mean maximum" forces signal values on the one hand and the minimum and "mean minimum" force signals on the other, in each case using a simple division expression as summarised.

Figure 5:
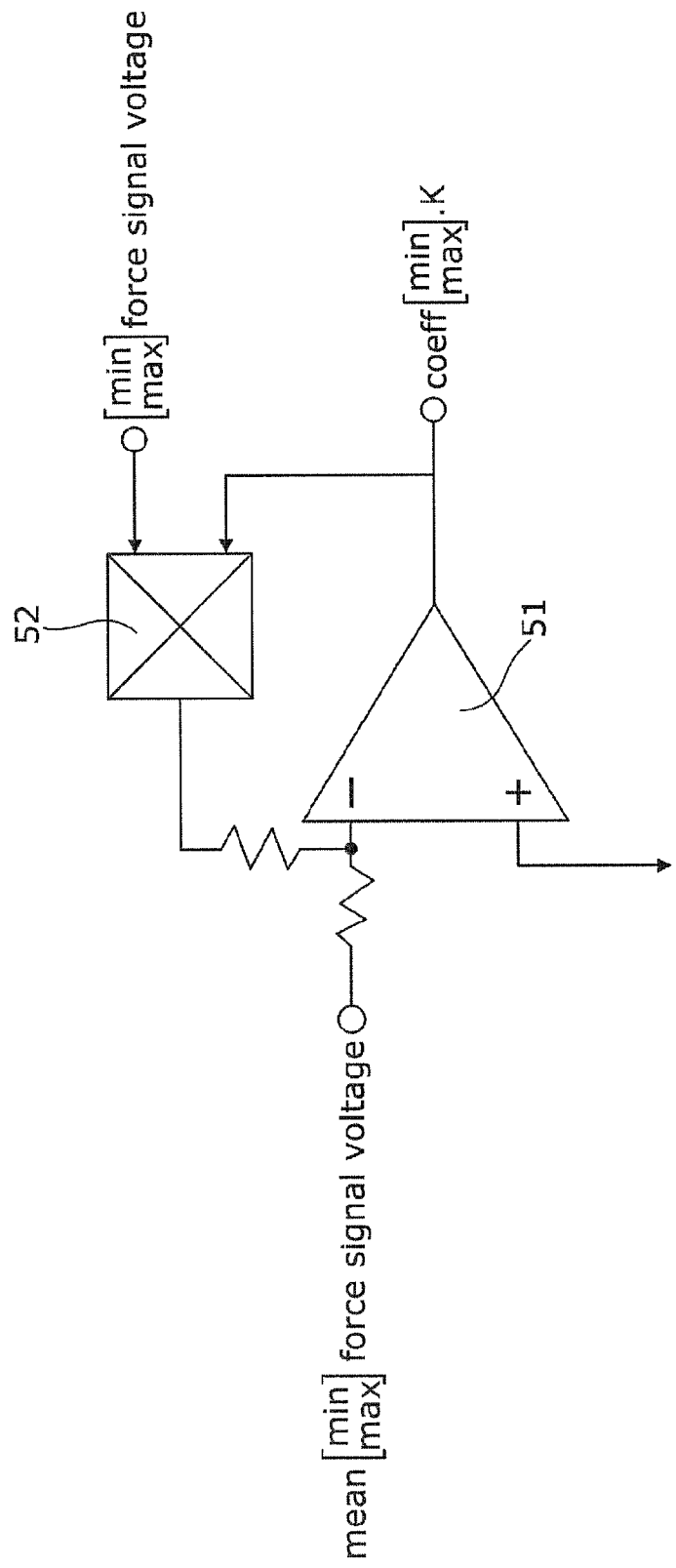
FIG. 5 shows in schematic form one embodiment of non-programmable device that may be used to derive signals from the outputs of sensors in the method of the invention.

Such comparisons may be effected using one or more programmable devices as mentioned; but this need not be the case. On the contrary, as is well known, a simple division-type signal magnitude comparison can be carried out using a permanently wired circuit such as an Op Amp and multiplier feedback combination. In such an arrangement as illustrated in FIG. 5 the mean maximum or minimum (as appropriate) signal voltage may be input to the inverting input of Op Amp 51 the non-inverting input of which is grounded.

The Op Amp output is fed back as one input to a multiplier 52 the other input of which is the maximum or minimum (as appropriate) force signal voltage. The output of the multiplier 52 is fed to the inverting input of the Op Amp 51. The net output is the maximum or minimum user coefficient, multiplied by Op Amp gain K. This signal may be used in the next stage of the method as described below.

The programmable or non-programmable device 33 uses the maximum and minimum user coefficients to calculate a user effectiveness score for each of the left and right pedal cranks 31 according to the following equations:

left score=$(W \times (\text{left coeff}_{min} \times \text{left coeff}_{max}) - M) \times 100$ right score=$(W \times (\text{right coeff}_{min} \times \text{right coeff}_{max}) - M) \times 100$ where:
W is a weighting factor that is based on a ratio between the effective force applied to the pedal cranks 31 and the total force applied to the pedal cranks 31 that is required to achieve the effective force; and M is a moderating factor to define an optimum user effectiveness score in the range of 70 to 80.

Simple multiplications such as those indicated may be performed by a multiplier as is familiar in engineering in the alternative to using a programmable device.

As it will be appreciated, the values of W and M will vary depending on the nature of the exercise machine. In the case of the Wattbike® 10 and the Wattbike Atom™ 50, the value of W may fall within the range of 0.8 to 1.8 and the value of M may fall within the range of −0.5 to −0.05.

The programmable device then uses the user effectiveness score for each of the left and right pedal cranks 31 to calculate an overall user effectiveness score according to the following equation:

$$\text{user effectiveness score} = \frac{(\text{left score} + \text{right score})}{2}$$

Such a derivation may take place by processing the left and right score signals using a programmable device or e.g. a combination of an Op Amp adder and a voltage divider.

The programmable or non-programmable device has a display and is configured to show the user effectiveness score.

The programmable or non-programmable device may also be configured to display other measured characteristics pertaining to the user's operation of the Wattbike® 10 or Wattbike Atom™ 50.

The programmable device 33 of the Wattbike® 10 shown in FIG. 3 is configured to display the user effectiveness score 38, as well as information pertaining to cadence 39, accurate power output by a user 40, heart rate 41, right 42 and left 43 leg power output percentages and duration of use 45 of the Wattbike® 10. The programmable device 33 is also configured to display on the screen the measured drive force against the temporal position of the pedal cranks 31 in the form of a polar view™ plot 44, such as the polar view™ shown in FIG. 2 and described above.

More or less information can be displayed on the programmable device 33. The information can also be displayed in arrangements that differ from that illustrated in FIG. 3. The information can be recorded, transmitted, downloaded, uploaded, stored and printed.

Figure 2:
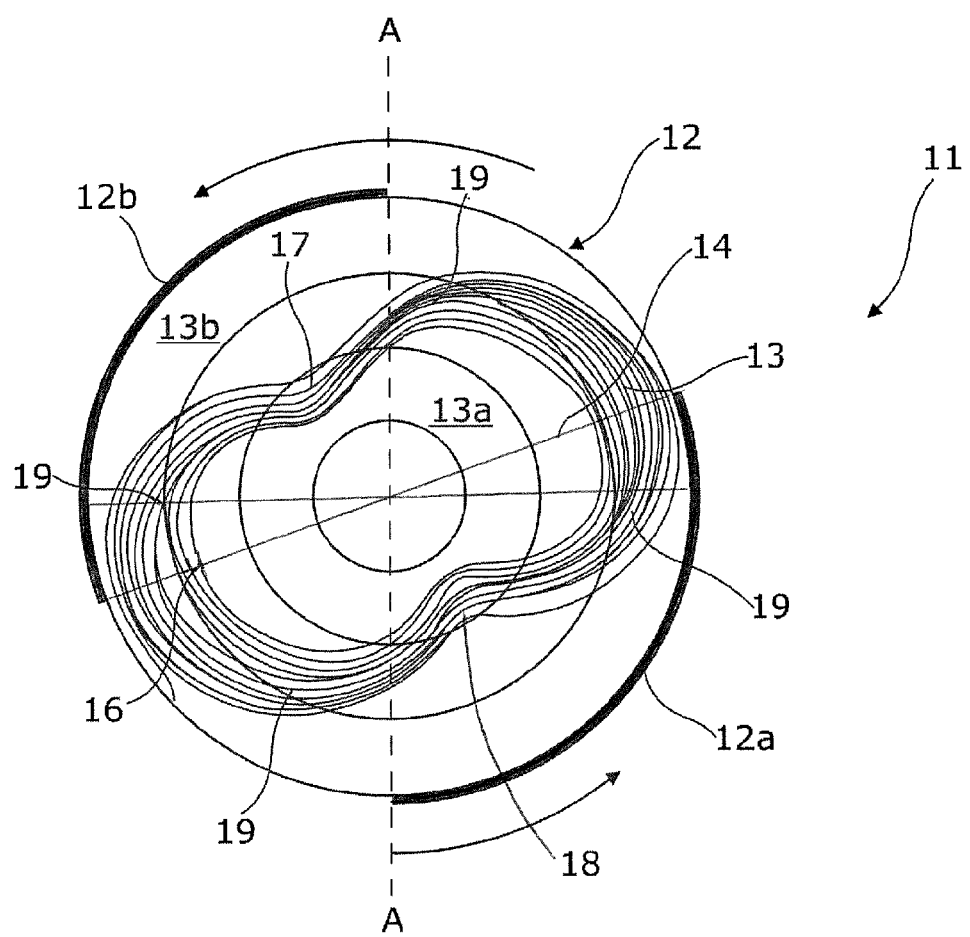
FIG. 2 shows a sample polar view™.

As a user starts riding on the Wattbike® 10 or the Wattbike Atom™ 50, he/she applies a drive force to the pedals 32, and hence the pedal cranks 31, pushing them down and pulling them up alternately on the right and left side. As each pedal crank 31 completes a revolution of 360°, a polar view™ (an example of which is shown in FIG. 2 and described above) indicative of the force generated and the temporal positions of the pedal cranks 31 is displayed on the programmable device 33. The drive force applied to the pedal cranks 31 is monitored and measured and signals indicative thereof generated about 100 times per second in the preferred embodiment shown, although other sampling rates are possible within the scope of the invention.

The programmable or non-programmable device derives, as explained, maximum and minimum user effectiveness coefficient signals for each drive member and then a user effectiveness score for each drive member before using the user effectiveness score for each drive member in order to derive an overall user effectiveness score in accordance with the equations described above.

An effectiveness score in the range of 70-80 is calculated if the user's cyclic operation of the Wattbike® 10 or the Wattbike Atom™ 50 is at or near optimal efficiency.

Over a certain monitoring period, more than one value of the user effectiveness score is generated. These values are analysed and a user can modify his/her training programme based on the effectiveness scores he/she has been outputting.

The programmable device is able to calculate the power generated in the pedal cranks 31 and display such power values.

A user may be wearing a chest strap, wrist strap, ankle strap or finger clip transmitting heart rate sensor. These devices generate user heart rate values which can be transmitted to the programmable device using various types of near-field communication. The programmable device 33 shown in FIG. 3 includes a display segment 41 that displays the instantaneously prevailing heart rate value.

The user effectiveness score, heart rate cadence, time and power values and the polar view™ data can each be recorded, displayed, printed, stored, downloaded, uploaded or transmitted to an electronic device such as a computer, tablet or smartphone.

The invention allows a user of an exercise machine having a pair of human limb-operable drive members coupled for cyclic movement to monitor, assess and compare the effectiveness of his/her cyclic technique. The invention provides an accurate figure that allows a user to determine how far the user's technique is from optimal effectiveness by displaying an effectiveness score. This effectiveness score can be shown in real time to the user, providing continuous feedback and thereby aiding in the user's training. Particularly in cycling, the invention enables a cyclist to improve his/her pedalling technique and, in turn, improve fitness, power, endurance and recovery aspects of training and competing.

The listing or discussion of an apparatus prior published apparatus in this specification should not necessarily be taken as an acknowledgment that the apparatus is part of the state of the art or is common general knowledge.

The invention claimed is:

1. A method of monitoring, by an electronic device, user effectiveness during performing cyclic movement using an exercise machine having a pair of human limb-operable drive members for performing the cyclic movement and one or more force sensors operatively coupled to the pair of drive members, the method comprising the steps of:

measuring and monitoring, using the one or more force sensors, user applied force to the pair of drive members during cyclic movement of the drive members and generating a plurality of force signal values;

receiving, by the electronic device operatively connected to the exercise machine, the plurality of force signal values generated;

allocating, by the electronic device, the plurality of force signal-signal values generated during a cycle of movement to one or other of the drive members based on points of load alternation during the cycle of movement;

generating, by the electronic device, for each of the drive members for the cycle of movement and using the plurality of force signal values allocated to each respective drive member, a maximum user effectiveness coefficient value and a minimum user effectiveness coefficient value, wherein generating, by the electronic device, the maximum user effectiveness coefficient value comprises:

determining a mean max force as a mean value of the plurality of force signal values generated for the cycle of movement over a predetermined segment of the cycle of movement in which a maximum magnitude force signal value is included as a data point of the plurality of force signal values generated in the predetermined segment, and comparing, using division, the mean max force with the maximum magnitude force signal value to generate the maximum user effectiveness coefficient-value; and wherein generating, by the electronic device, the minimum user effectiveness coefficient value comprises:

determining a mean min force as a mean value of the plurality of force signal values generated for the cycle of movement over a predetermined segment of the cycle of movement in which a minimum magnitude force signal value is included as a data point of the plurality of force signal values generated in the predetermined segment, and comparing, using division, the mean min force with the minimum magnitude force signal value to generate the minimum user effectiveness coefficient-value;

calculating, by the electronic device, a user effectiveness score for each of the drive members, using the generated maximum and minimum user effectiveness coefficient values of the corresponding drive member;

determining, by the electronic device and using the calculated user effectiveness scores, an overall user effectiveness score indicative of user effectiveness in driving cyclic movement of the drive members; and outputting, by the electronic device, the overall user effectiveness score.

2. The method according to claim 1 wherein the step of comparing, using division, the mean max force with the maximum magnitude force signal value to generate the maximum user effectiveness coefficient value comprises applying the following equation:

$$coeff_{max} = \frac{\text{mean max force}}{\text{maximum magnitude force value}}$$

where:
$coeff_{max}$ is the maximum user effectiveness coefficient value;
wherein, in the mean max force calculation, the predetermined segment is centered on the maximum magnitude force value such that the maximum magnitude force value is a median data point of the plurality of force signals measured in the predetermined segment; and
the step of comparing, using division, the mean min force with the minimum magnitude force signal value to generate the minimum user effectiveness coefficient value comprises applying the following equation:

$$coeff_{min} = \frac{\text{minimum magnitude force value}}{\text{mean min force}}$$

where:
$coeff_{min}$ is the minimum user effectiveness coefficient value;
wherein, in the mean min force calculation, the predetermined segment is centered on the minimum magnitude force value such that the minimum magnitude force value is a median data point of the plurality of force signals measured in the predetermined segment.

3. The method according to claim 2 wherein the plurality of force signal values are relative to angular positions of rotation of a drive wheel, and the predetermined segment is a segment of 45°.

4. The method according to claim 3 further comprises the step of: generating, by the electronic device, a display illustrating the user applied force to the pair of drive members as it is allocated to the drive members for each cycle of movement.

5. The method according to claim 1 wherein generating the plurality of force signal values comprises periodically generating the plurality of force signal values.

6. The method according to claim 5 wherein generating the plurality of force signal values comprises measuring, by the one or more force sensors, tension in a drive chain driven by the pair of drive members.

7. The method according to claim 5 wherein the periodicity of generation of the plurality of force signal values is 100 Hz.

8. The method according to claim 1 wherein the pair of drive members drive a drive train of the exercise machine that transfers or dissipates cyclic effort, and
wherein the step of measuring and monitoring user applied force to the pair of drive members during the cyclic movement of the drive members comprises measuring a force generated in the drive train in at least one location and generating the plurality of force signals indicative thereof.

9. The method according to claim 8 wherein the drive train includes a magnetic and/or electromagnetic resistor of cyclic effort, and the method further comprising: switching or adjusting, by the electronic device, cyclic resistance using the magnetic and/or electromagnetic resistor.

10. The method according to claim 8 wherein the drive train includes an axle the method includes measuring a value of torque in the axle and generating one or more signals indicative thereof.

11. The method according to claim 1 the step of allocating the plurality of force signal values generated during the cycle of movement to one or other of the drive members is based on determining which of the drive members provide a dominant proportion of the user applied force during the cycle of movement.

12. The method according to claim 1 further including the step of modifying, by the electronic device, cyclic movement of the drive members based on the overall user effectiveness score.

13. The method according to claim 1 wherein the exercise machine further comprises a respective pedal or handle that is rotatably secured to each said drive member, the drive members coupled to drive rotation of a drive wheel of the exercise machine and mutually subtending an angle of 180°.

14. The method according to claim 1 wherein the step of calculating a user effectiveness score for each of the drive members additionally involves using a predetermined weighting factor with the maximum and minimum user effectiveness coefficient values generated for each of the drive members, the weighting factor being based on a ratio for the exercise machine between an effective force applied to the drive members and a total force applied to the drive members that is required to achieve the effective force.

15. The method according to claim 1 wherein the step of calculating a user effectiveness score signal for each of the drive members additionally involves using a predetermined moderation factor such that the user effectiveness score for each drive member falls within an optimum range between 70 and 80.

16. The method according to claim 1 further comprising the step of: generating, by the electronic device, indicia representative of the overall user effectiveness score signal-over a monitoring period, analysing analyzing, by the electronic device, the overall user effectiveness score and detecting, by the electronic device, changes in the overall user effectiveness score during the monitoring period.

17. The method according to claim 1 further including the step of: modifying, by the electronic device, a user training program based on the overall user effectiveness score for one or more cycles of movement of the drive members.

18. An exercise machine comprising:
a pair of human limb-operated drive members coupled for cyclic movement;
one or more force sensors operatively coupled to the pair of drive members; and
an electronic device having at least one sensory indicator, operatively connected to the one or more force sensors, wherein the electronic device implements the method of claim 1 to determine an overall user effectiveness score, and
outputs the overall user effectiveness score via the sensory indicator.

19. The exercise machine according to claim 18 wherein the electronic device is selected from a group consisting of a laptop, a tablet, a smartphone, a personal digital assistant (PDA), and a monitor forming part of the exercise machine.

* * * * *